United States Patent [19]

Corey

[11] 3,974,183
[45] Aug. 10, 1976

[54] REDUCTION OF TRANS-1-(2-CARBOXYMETHYL-3-HYDROXY-5-p-PHENYLBENZOYLOXYCYCLOPENTYL)-1-OCTEN-3-ONE-γ-LACTONE

[76] Inventor: Elias J. Corey, Pfizer Inc., 235 E. 42nd St., New York, N.Y. 10017

[22] Filed: July 12, 1974

[21] Appl. No.: 487,885

Related U.S. Application Data

[60] Division of Ser. No. 324,511, Jan. 17, 1973, Pat. No. 3,867,460, which is a continuation-in-part of Ser. No. 117,748, Feb. 22, 1971, abandoned.

[52] U.S. Cl. .......................................... 260/343.3 R
[51] Int. Cl.$^2$ ........................................ C07D 307/00
[58] Field of Search ................................ 260/343.3

[56] References Cited
UNITED STATES PATENTS 3,055,945  9/1962  Honeycutt .................... 260/606.5 B

OTHER PUBLICATIONS

Corey et al., *J.A.C.S.* 91:5675, 1969.
Brown et al., *J.A.C.S.* 92:709 (1970).

*Primary Examiner*—Richard J. Gallagher
*Attorney, Agent, or Firm*—Connolly and Hutz

[57] ABSTRACT

A process for reducing trans-1-(2-carboxymethyl-3-hydroxy-5-acyloxycyclopentyl)-1-octen-3-one-γ-lactone to the corresponding 3-ol which makes use of trihydrocarbylborohydride reagents, some of which are new, e.g. lithium 2-thexyl-8-methyl-2-borabicyclo-[3,3,1]nonylhydride. A new process for producing this and other lithium thexyl-dihydrocarbylborohydrides which comprises contacting a thexyl-dihydrocarbylborane with an organo-lithium compound having a β-hydrogen atom.

9 Claims, No Drawings

REDUCTION OF TRANS-1-(-CARBOXYMETHYL-3-HYDROXY-5-p-PHENYLBENZOYLOXYCYCLOPENTYL)-1-OCTEN-3-ONE-Γ-LACTONE

CROSS-REFERENCE TO RELATED APPLICATIONS

This application is a division of application Ser. No. 324,511 filed Jan. 17, 1973 (now U.S. Pat. No. 3,867,460) which in turn, is a continuation-in-part of application Ser. No. 117,748 filed Feb. 22, 1971 and now abandoned.

BACKGROUND OF THE INVENTION

This invention relates to prostaglandin synthesis. The synthesis of prostaglandins $E_1$, $E_2$, $F_1 \alpha$, and $F_2 \alpha$ in optically active form constituted notable achievements (E. J. Corey, et al., *J. Amer. Chem. Soc.* 92:397, 1970; 42:2586, 1970; and earlier papers). These synthetic sequences are particularly characterized by mild and specific reaction conditions. Further progress in prostaglandin research was severely encumbered by the lack of a stereoselective means for the introduction of the chiral (asymmetric) carbon which bears the sidechain secondary alcohol function of the prostaglandins (C-15). This chiral center is labelled in the formula below for prostaglandin $E_1$.

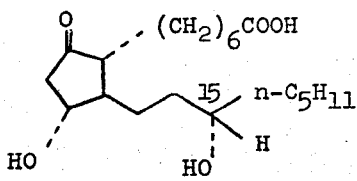

In the published procedure (E. J. Corey, et al., *J. Amer. Chem. Soc.* 91:5675, 1969) using zinc borohydride as the reducing agent, a 1:1 mixture of epimers is obtained when Ketone I (a trans-3-enone lactone) is reduced to the corresponding trans-3-enol (Alcohol II and III). Only one of these epimers (Alcohol II), which is the S-configuration isomer, is suitable for conversion to natural prostaglandins.

SUMMARY OF THE INVENTION

The present invention comprises a process for the stereoselective reduction of the above key intermediate (Ketone I) in the synthesis of optically active prostaglandins; namely, it comprises the reduction of trans-1-(2-carboxymethyl-3-hydroxy-5-acyloxy-cyclopentyl)-1-octen-3-one γ-lactone to the corresponding 3-ol by contacting said 3-one in inert solvent and under inert atmosphere with at least equimolar proportions of a lithium trihydrocarbyl borohydride and a Lewis base at between about −50° and −150°C. until the reaction is substantially complete. A reaction temperature of between about −78° and −105°C. is especially preferred. Stereoselectivity is enhanced at low temperatures. A ratio of as high as 4:1 of the desired S-configuration isomer to the R-configuration isomer is obtained by the process of this invention in contrast to a ratio of only 1:1 by prior art methods.

Preferred borohydrides for the new reduction reaction are:
1. lithium 2-thexyl-8-methyl-2-borobicyclo[3,3,1-]nonylhydride

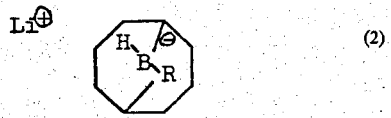

wherein R is alkyl having from 1 to 6 carbon atoms, cycloalkyl having from 5 to 6 carbon atoms, or phenyl;

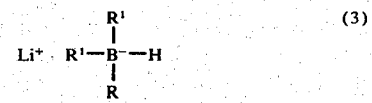

wherein $R^1$ is cycloalkyl having from 5 to 6 carbon atoms and R is alkyl having from 1 to 6 carbon atoms, cycloalkyl having from 5 to 6 carbon atoms, or phenyl;
4. lithium perhydro-9b-borophenalyhydride; and

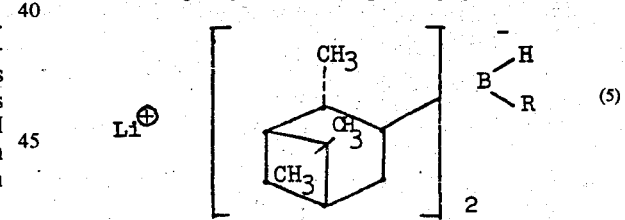

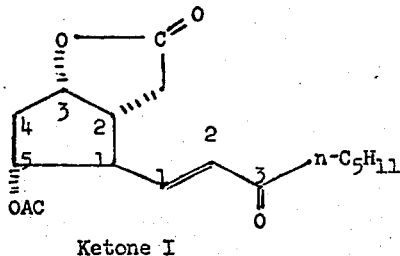

Ketone I

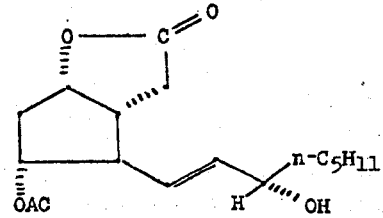

Alcohol II

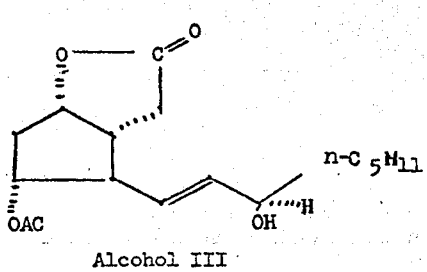

Alcohol III wherein R is alkyl having from 1 to 6 carbon atoms, cycloalkyl having from 5 to 6 carbon atoms, or phenyl.

A wide variety of Lewis bases may be employed in the reaction, such as Lewis bases containing oxygen, nitrogen, sulfur or phosphorus, e.g. tertiary amines, or other proton acceptors. The choice of Lewis base is not critical, but hexamethyl phosphorus triamide is especially preferred. Any Lewis base which serves to suppress competing C=C reductions may be employed.

The acyloxy moiety may represent a wide variety of esters, with large ester groups such as p-phenylbenzoate ester being especially preferred although acetate ester may be used. In fact, other types of protecting groups may be employed such as 2-tetrahydropyranyl or N,N-biphenylcarbamoyloxy. The protecting group employed is not a critical part of the invention.

The present invention further comprises, as new compositions of matter:

1. lithium 2-thexyl-8-methyl-2-borobicyclo[3,3,1-]nonylhydride

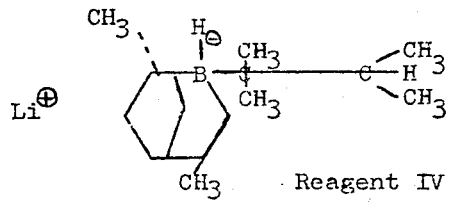

Reagent IV 2. a borohydride of the formula:

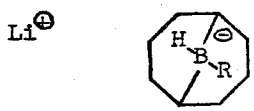

wherein R is alkyl having from 1 to 6 carbon atoms, cycloalkyl having from 5 to 6 carbon atoms, or phenyl.

An especially preferred compound of this type is lithium 9-thexyl-9-borabicyclo[3,3,1]nonylhydride (Reagent V).

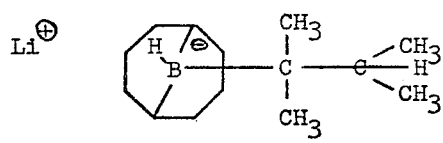

3. a borohydride of the formula:

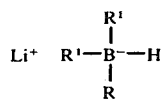

wherein $R^1$ is cycloalkyl having from 5 to 6 carbon atoms and R is alkyl having from 1 to 6 carbon atoms, cycloalkyl having from 5 to 6 carbon atoms, or phenyl.

The present invention further comprises the process for preparing those of the above mentioned new borohydrides wherein R is thexyl, by contacting a thexyl-dihydrocarbylborane in inert solvent with at least an equimolar proportion of an organo-lithium compound capable of donating a $\beta$ hydrogen atom at a temperature of from about −20° to +20°C. until the reaction is substantially complete. t-Alkyl lithium compounds having 4 to 8 carbon atoms are preferred and t-butyl lithium is especially preferred. A reaction temperature of 0°C. is especially preferred. This reaction consists of the hydrogenation of the borane with a $\beta$ hydrogen atom supplied by an organo-lithium compound capable of giving up such a $\beta$ hydrogen atom. A wide variety of thexyl-dihydrocarbylboranes may be employed in this reaction to produce useful reducing agents, but 2-thexyl-8-methyl-2-borabicyclo[3,3,1]nonane (Reagent VI) and 9-thexyl-9-borabicyclo[3,31]nonane (Reagent VII) and a borane of the formula:

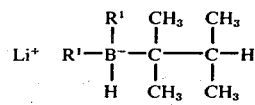

wherein $R^1$ is cycloalkyl having from 5 to 6 carbon atoms or phenyl; are especially preferred.

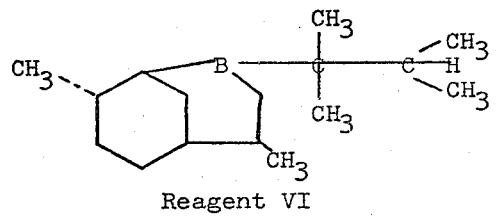

Reagent VI

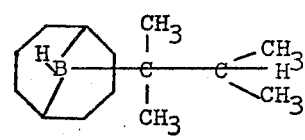

Reagent VII

DETAILED DESCRIPTION OF THE INVENTION

Preparation of trihydrocarbylboranes used in producing trihydrocarbylborohydrides is performed by the general methods of Zweifel and Brown (*J. Amer. Chem. Soc.*, 85:2066, 1963) and Brown and Pfaffenberger (*J. Amer. Chem. Soc.*, 89:5475, 1967). However, in the case of Reagent VI these workers used d-limonene in the reaction. It has been found that d,1-limonene works equally well, and because of greater ease in obtaining the racemic compound, its use is preferred.

Those trihydrocarbylboranes having a thexyl group are converted to the corresponding borohydrides by the following new procedure: Thexyl dihydrocarbylborane in reaction-inert solvent is cooled and stirred in an ice-bath over an atmosphere of dry nitrogen. Then a solution of t-butyllithium, or other organolithium compound having a $\beta$ hydrogen atom, is added dropwise. The solution is stirred at about 0°C. for one hour, to obtain the thexyl dihydrocarbylborohydride.

The preparation of the thexyl dihydrocarbylborohydride can be carried out in any of a variety of reaction-inert solvents, but tetrahydrofuranpentane is particularly preferred.

The reduction of Ketone I (above) to Alcohols II and III is best carried out in an inert solvent such as tetrahydrofuranpentane; ether; 1,2-dimethoxyethane; or various combinations of these solvents, and in an inert atmosphere such as dry nitrogen or argon. The solvent should be one that remains fluid at the reaction temperature selected.

The Ketone I in tetrahydrofuran//pentane solution, for example, is added to the reaction vessel. A Lewis base, such as hexamethylphosphorus amide, is then added to the solution. The amount used should be in at least a 1:1 molar ratio with Ketone I, but large excesses of up to 20 fold are permissible. Other Lewis bases such as tertiary amines can also be effectively used in this reaction. Then the reducing agent, e.g. Reagent IV or V is added, also preferably in at least a 1:1 molar ratio with Ketone I, and the reaction is allowed to proceed at about −100° to −105°C. A temperature as high as −78°C. will yield a useful proportion of the desired isomer, but reaction temperatures substantially higher than −78°C. cause the production of a large amount of the unwanted R-configuration isomer (Alcohol III). Temperatures as low as −150°C. can be tolerated. When the reaction is substantially complete, the reaction is quenched with acid, e.g. 1N-aqueous HCl and the mixture is diluted with water and extracted with inert solvent, e.g. ether. Evaporation of solvent after drying affords a >90% yield of a mixture of Alcohols II and III in a ratio of as high as 4:1 depending upon the reducing agent employed. The alcohols may be separated by conventional chromatography using silica gel.

A variety of lithium trihydrocarbylborohydrides may be used as reducing agents in the reduction of Ketone I to Alcohol II and III, but those which have large hydrocarbyl moieties e.g., thexyl and limonyl attached to the boron, are especially effective in producing the desired ratio of Alcohol II to Alcohol III.

Other lithium trihydrocarbylborohydride reducing agents which are useful in this respect, and which are new compounds of this invention, are those of the formula:

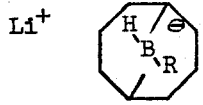

wherein R is alkyl (i.e. having from 1 to 8 and preferably from 1 to 6 carbon atoms), cycloalkyl of 5 to 6 carbon atoms, or phenyl. Such compounds are prepared by the direct reaction of RLi to the corresponding borane (see Knights and Brown, *J. Amer. Chem. Soc.* 90:5280, 1968 for borane preparation). In the case where R = thexyl, the reaction involving the β hydrogen atom of an organolithium compound should be employed, as previously described.

Other lithium trihydrocarbylborohydride reducing agents, also new compounds of this invention, are of the formula:

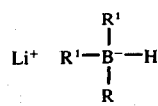

wherein $R^1$ is cycloalkyl of 5 to 6 carbon atoms and R is alkyl having from 1 to 6 carbon atoms, cycloalkyl of 5 to 6 carbon atoms or phenyl. These reagents are prepared by the direct reaction of RLi with appropriate boranes such as are described by Brown in Hydroboration, W. A. Benjamin, Inc., New York (1962).

Still another example of a lithium trihydrocarbylborohydride reducing agent useful in the new process of this invention is lithium perhydro-9b-boropenalylhydride. The preparation of this borohydride is given by Brown and Dickason, *J. Amer. Chem. Soc.* 92:709 (1970).

Other reagents which have been used to reduce Ketone I to Alcohols II and III are of the formula:

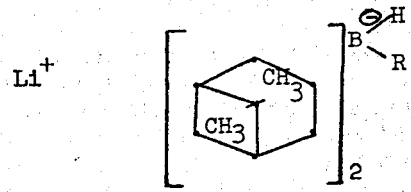

wherein R is alkyl having from 1 to 6 carbon atoms, cycloalkyl having from 5 to 6 carbon atoms, or phenyl. These compounds are made from the reaction of RLi and boranes as prepared by Brown, et al. *J. Amer. Chem. Soc.* 86:1071 (1964).

The following examples are given by way of illustration and are not intended to depart from the spirit and scope of the appended claims.

EXAMPLE I

A 50-ml. round-bottomed flask equipped with a magnetic stirring bar was closed with a rubber septum and flamed in a stream of dry nitrogen. It was subsequently cooled in a bath at −10° and was thereafter maintained over an atmosphere of nitrogen by the balloon technique. In the flask was placed a solution of diborane in tetrahydrofuran (25.0 ml., 26.25 mmol), and 2,3-dimethyl-2-butene (26.25 mmol, 2.20 g., 3.1 ml.) was added drop by drop from a hypodermic syringe in the course of 15.0 min. The resulting homogeneous solution was stirred for a few minutes and was then ready to use. The molarity estimated by the measurement of the gas evolved on decomposition of aliquots with tetrahydrofuran-water-ethylene glycol (1:1:1) was 0.931.

In a 100-ml. round-bottomed flask equipped with a magnetic stirring bar and flushed with dry nitrogen was placed dry tetrahydrofuran. The flask was then cooled and was efficiently stirred in an ice bath. Then 10.0 ml. each of 0.931 M solutions of thexylborane and (±) or d-limonene in tetrahydrofuran were added simultaneously and at the same rate from identical 10.0 ml. syringes in the course of 50 min. with the aid of a double syringe pump. After stirring for 1.0 hr. at 0°, the solution was ready for use in the next step of the reaction.

The solution of the borane VI (9.31 mmol) was stirred in an ice-bath over an atmosphere of dry nitrogen. Then a solution of t-butyllithium (9.3 mmol, 4.27 ml.) in pentane was added drop by drop in the course of 5.0 min. A transient canary yellow color was produced and disappeared as each drop fell into the reaction vessel. The resulting colorless, homogeneous solution was then stirred for 1.0 hr. at 0° prior to use. The product obtained was borohydride IV, lithium 2-thexyl-8-methyl-2-borabicyclo[3,3,1]nonylhydride.

The infrared absorption spectrum of this solution showed a broad, medium intensity absorption at 4.90 μ(2041 cm$^{-1}$) due to ⁻B—H. Such an absorption is exhibited by trialkylborohydrides (see H. C. Brown and W. C. Dickason, *J. Amer. Chem. Soc.*, 92, 709, 1970, and P. Binger, G. Benedikt, G. W. Rotermound, and R. Koster, *Ann.*, 717, 21, 1968).

The above procedure was repeated substituting 9-thexyl-9-borabicyclo-[3,3,1]nonane (prepared by the method of knights and Brown, *J. Amer. Chem. Soc.* 90:5280, 1968), for the above mentioned borane, to produce 9-thexyl-9-borabicyclo[3,3,1]nonylhydride.

EXAMPLE II

In a 25-ml. round-bottomed flask equipped with a magnetic stirring bar was placed Ketone I (111.2 mg., 0.25 mmol). The flask was then closed with a rubber septum, flushed with dry nitrogen, and subsequently maintained under an atmosphere of nitrogen. Then dry tetrahydrofuran (2.5 ml.) was added; the solution was cooled and stirred in a bath at −100° to −105°, and hexamethylphosphorus amide (5.0 mmol, 809 mg., 0.91 ml.) was introduced from a hypodermic syringe. Finally, the solution of borohydride IV described in the previous example (7.5 ml., 1.31 mmol) was added drop by drop in the course of 15 minutes. The reaction was allowed to proceed for 3.0 hr. at −100° to −105° and was then quenched by the addition of 7 ml. of 1N-hydrochloric acid and warmed to −10°C. It was then diluted with ice water (30 ml.) and extracted with ether (4 × 30 ml.). The extracts were then combined, washed successively with water (3 × 15 ml.) and a saturated sodium chloride solution (2 × 10 ml.), dried (anhydrous MgSO$_4$), filtered, and evaporated at room temperature in vacuo. The residual oil was spotted on two tlc plates (2 × 200 × 200 mm), and the plates were developed two or three times with ethyl acetate-benzene (1:3). The bands corresponding to the alcohols 2 and 3 were separately extracted with ethyl acetate-methanol (95:5), and the extracts were evaporated at room temperature in vacuo. They were redissolved in small amounts of ethyl acetate and washed with distilled water to remove the small amounts of entrained silica. These solutions were then dried (anhydrous MgSO$_4$) and evaporated afford Alcohol II (82.61 mg) and Alcohol III (20.31 mg.). The total yield of II and III was 92.37%. The nuclear magnetic resonance and infrared spectra of II and III thus prepared were identical with those of authentic samples.

EXAMPLE III

Following the procedures of Example II the reducing agents given below were used to reduce Ketone I to Alcohol II and Alcohol III. The ratio of Alcohol II to Alcohol III obtained in the reductions was from 2.8 to 3.0.

Reducing Agent

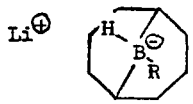

wherein R is methyl, t-butyl, thexyl and phenyl.

These reducing agents were prepared by the methods of Knights and Brown, *J. Amer. Chem. Soc.* 90:5280 (1968) followed by conventional RLi addition, except for the case of R = thexyl which was prepared in Example I.

EXAMPLE IV

Following the procedures of Example II the reducing agents given below were used to reduce Ketone I to Alcohol II and Alcohol III. The ratio of Alcohol II to Alcohol III obtained in the reductions was from 1.8 to 2.2.

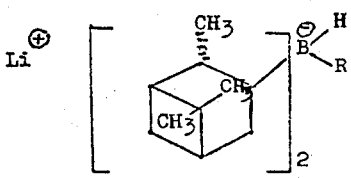

wherein R is methyl, isopropyl, t-butyl and cyclohexyl. For preparation of the borohydrides see Brown, et al., *J. Amer. Chem. Soc.* 86:1071 (1964), followed by conventional RLi addition.

EXAMPLE V

Following the procedures of Example II the reducing agents given below were used to reduce Ketone I to Alcohol II and Alcohol III. The ratio of Alcohol II to Alcohol III obtained in the reductions was from 1.8 to 2.8.

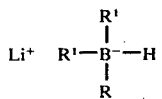

wherein R$^1$ is cyclohexyl and R is methyl, t-butyl and phenyl. These reducing agents are prepared by the general methods of Brown in *Hydroboration*, published by W. A. Benjamin, Inc., New York, 1962, followed by conventional RLi addition.

EXAMPLE VI

Following the procedures of Example II, lithium perhydro-9b-boraphenalylhydride was employed as the reducing agent. A ratio of Alcohol II to Alcohol III of 2.1:1 was obtained. This reducing agent was prepared by the method of Brown and Dickason, *J. Amer. Chem. Soc.* 92:709 (1970), followed by conventional RLi addition.

EXAMPLE VII

The procedure of Example I was repeated using 0.01 mole (10 mls of a 1 molar solution in tetrahydrofuran) of borane to which 0.03 mole cyclopentene (2.04 g) was added dropwise at −20°C. under a nitrogen atmosphere. After stirring for 1 hour at 0°, 0.01 mole of t-butyllithium (7.14 ml of 1.4 molar solution in pentane) was added dropwise over 10 minutes and the solution stirred for an additional 1 hour at 0° to give the tricyclopentyl lithium borohydride (0.5 molar solution).

EXAMPLE VIII

To a cooled solution of 0.14 g ketone (I) in 5 ml tetrahydrofuran at −75° was added 0.5 ml of tricyclopentyl borohydride (1.23 molar solution) of Example VII over a period of 15 minutes. The reaction was stirred an additional 15 minutes and quenched by adding 3 ml of 40% acetic acid. The reaction was allowed to come to room temperature and extracted with CH$_2$Cl$_2$. The organic layer was washed with brine, dried (Na$_2$SO$_4$) and concentrated. The residue chromatographed on silica gel afforded 80 mg alcohol II, 39 mg alcohol III and 6 mg mixed fraction of alcohols II and III.

What is claimed is:

1. A process for the reduction of trans-1-(2-carboxymethyl-3-hydroxy-5-p-phenylbenzoyloxycyclopentyl-1-octen-3-one-γ-lactone to the corresponding 3-ol which comprises the step of contacting said 3-one in an inert solvent under an inert atmosphere at between about −50° and −150°C. with at least about equimolar proportions of a Lewis base which suppresses competing C=C reductions and a borohydride selected from the group consisting of:

lithium 2-thexyl-8-methyl-2-borabicyclo/3,3,1-/nonylhydride;

lithium perhydro-9b-borophenalylhydride;

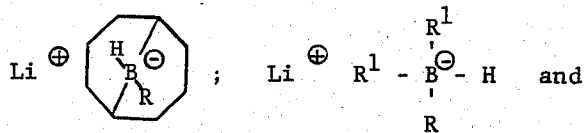

wherein R¹ is cycloalkyl having from 5 to 6 carbon atoms and R is alkyl having from 1 to 6 carbon atoms, cycloalkyl having from 5 to 6 carbon atoms or phenyl until said 3-one is substantially reduced to said 3-ol.

2. The process of claim 1 wherein said borohydride is lithium 2-thexyl-8-methyl-2-borabicyclo[3,3,1-]nonylhydride.

3. The process of claim 1 wherein said borohydride is a compound of the formula

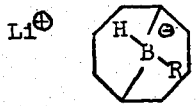

wherein R is alkyl having from 1 to 6 carbon atoms, cycloalkyl having from 5 to 6 carbon atoms or phenyl.

4. The process of claim 3 wherein said borohydride is 9-thexyl-9-borabicyclo[3,3,1]nonylhydride.

5. The process of claim 1 wherein said borohydride is a compound of the formula

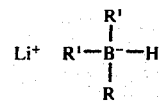

wherein R¹ is cycloalkyl having from 5 to 6 carbon atoms and R is alkyl having from 1 to 6 carbon atoms, cycloalkyl having from 5 to 6 carbon atoms or phenyl.

6. The process of claim 1 wherein said borohydride is lithium perhydro-9b-boraphenalylhydride.

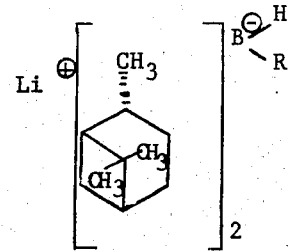

7. The process of claim 1 wherein said borohydride is a compound of the structure

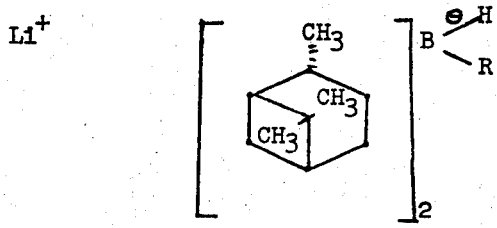

wherein R is alkyl having from 1 to 6 carbon atoms, cycloalkyl having from 5 to 6 carbon atoms or phenyl.

8. The process of claim 1 wherein said contacting is conducted between about −78° and −105°C.

9. The process of claim 1 wherein said Lewis base is hexamethyl phosphorus triamide.

* * * * *